United States Patent [19]

Phillips et al.

[11] Patent Number: 4,814,325
[45] Date of Patent: Mar. 21, 1989

[54] DITHIACYCLOALKENYL PHOSPHORIC ESTER PESTICIDES

[75] Inventors: Richard B. Phillips, Riverbank, Calif.; David M. Roush, Princeton, N.J.

[73] Assignee: FMC Corporation, Philadelphia, Pa.

[21] Appl. No.: 908,493

[22] Filed: Sep. 17, 1986

Related U.S. Application Data

[63] Continuation-in-part of Ser. No. 741,990, Jun. 6, 1985, abandoned.

[51] Int. Cl.⁴ ............... A01N 43/32; A01N 43/24; C07D 339/00; C07D 339/08
[52] U.S. Cl. ........................................ 514/97; 549/5
[58] Field of Search ............................ 549/5; 514/97

[56] References Cited

U.S. PATENT DOCUMENTS

| 2,864,826 | 12/1958 | Diveley et al. ............ 549/5 |
| 3,071,594 | 1/1963 | Enders et al. ............ 549/5 |

FOREIGN PATENT DOCUMENTS 767950  2/1957  United Kingdom ............ 514/97

OTHER PUBLICATIONS

Howard et al., *J. Am. Chem Soc.*, 82, 158, (1960).

Primary Examiner—Mary C. Lee
Assistant Examiner—Mary S. Howard
Attorney, Agent, or Firm—Stanford M. Back; H. R. Ertelt

[57] ABSTRACT

Dithiacycloalkenyl phosphoric esters of the following formula are effective for the control of soil and foliar insects, acarids and nematodes:

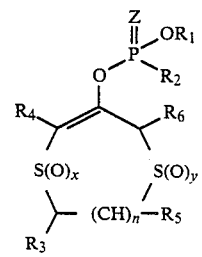

wherein
$R_1$ is lower alkyl;
$R_2$ is lower alkoxy or lower alkylthio;
$R_3$ is hydrogen, lower alkyl or phenyl;
$R_4$, $R_5$ and $R_6$ are independently hydrogen or lower alkyl;
Z is oxygen or sulfur;
x is 0 or 1;
y is 0, 1 or 2; and
n is 0, 1 or 2.

27 Claims, No Drawings

DITHIACYCLOALKENYL PHOSPHORIC ESTER PESTICIDES

This is a continuation in part of application Ser. No. 741,990, filed June 6, 1985, now abandoned.

This invention is in the field of agricultural chemicals. More specifically, the invention relates to novel organic phosphate and thiophosphate esters, agricultural compositions containing the novel esters, and the use of the esters to control a variety of agricultural pests.

Esters within the scope of this invention are described by the following structural formula:

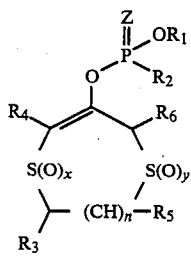

in which
R$_1$ is lower alkyl;
R$_2$ is lower alkoxy or lower alkylthio;
R$_3$ is hydrogen, lower alkyl or phenyl;
R$_4$, R$_5$ and R$_6$ are independently hydrogen or lower alkyl;
Z is oxygen or sulfur;
x is 0 or 1; and
y and n are independently 0, 1 or 2.

In the aforesaid description and wherever employed in this application the term "lower alkyl" means a straight or branched chain containing 1 to 6, preferably 1 to 4, carbon atoms, while "lower alkoxy" and "lower alkylthio" contemplate bonded to oxygen and sulfur, respectively, a straight or branched chain containing 1 to 6, preferably 1 to 4, carbon atoms.

Compounds within the scope of this invention are effective as insecticides and acaricides when applied to the foliage of plants or, systemically, when applied to the soil in the vicinity of plants. They are also active directly against soil-dwelling insects when applied to or incorporated into the soil. Furthermore, esters of this invention are active in the soil as nematicides.

Within the aforesaid description the esters of greatest interest are those wherein R$_3$ and R$_5$ are independently hydrogen or methyl, R$_4$ and R$_6$ are hydrogen, y is 0, x+y is less than 3, and n is 1. Excellent foliar and systemic activity is seen in compounds wherein R$_2$ is lower alkoxy, while those compounds in which R$_1$ and R$_2$ are other than methyl and methoxy, respectively, display pronounced activity as soil insecticides and nematicides.

Overall, specific esters of interest include O,O-diethyl O-(1,3-dithiacyclohex-4-en-5-yl)phosphorothioate, dimethyl 1,4-dithiacyclohept-5-en-6-yl phosphate, diethyl 1,4-dithiacyclohept-5-en-6-yl phosphate, O,O-diethyl O-(1,4-dithiacyclohept-5-en-6-yl)phosphorothioate, diethyl 2-methyl-1,4-dithiacyclohept-5-en-6-yl phosphate, diethyl 3-methyl-1,4-dithiacyclohept-5-en-6-yl phosphate, diethyl 1-oxo-1,4-dithiacyclohept-5-en-6-yl phosphate, dimethyl 1-oxo-1,4-dithiacyclohept-5-en-6-yl phosphate, 5-methyl-1,4-dithiacyclohept-5-en-6-yl phosphate, 7-methyl-1,4-dithiacyclohept-5-en-6-yl phosphate dimethyl 2-methyl-1,4-dithiacyclohept-5-en-6-yl phosphate, and dimethyl 3-methyl-1,4-dithiacyclohept-5-en-6-yl phosphate.

Attractive insecticidal and acaricidal activity is exhibited by diethyl 1,4-diethiacyclohept-5-en-6-yl phosphate, diethyl 1-oxo-1,4-dithiacyclohept-5-en-6-yl phosphate, and dimethyl 1-oxo-1,4-dithiacyclohept-5-en-6-yl phosphate.

Prominent soil insecticidal and nematicidal activity is seen in diethyl 1,4-dithiacyclohept-5-en-6-yl phosphate, diethyl 2-methyl-1,4-dithiacyclohept-5-en-6-yl phosphate, diethyl 3-methyl-1,4-dithiacyclohept-5-en-6-yl phosphate, and diethyl 1-oxo-1,4-dithiacyclohept-5-en-6-yl phosphate.

The phosphoric esters of this invention are prepared by variations within the skill of the art of general techniques disclosed in readily available technical literature. For example, *Synth.*, 184 (1979); *J. Am. Chem. Soc.*, 82, 158 (1960); and *Ann.*, 624, 79 (1959). In many cases a close precursor of the desired ester is a dithiacycloalkanone.

The preparation of esters within the scope of this invention will be clarified by reference to the following Examples.

EXAMPLE 2

O,O-Diethyl O-(1,3-dithiacyclohex-4-en-5-yl)Phosphorothioate

To a stirred mixture of 20 ml (0.27 mole) of paraformaldehyde solution (37.1%) and 49.1 g (0.53 mole) of mercaptoacetic acid was added 5 ml of concentrated hydrochloric acid. This mixture was stirred at 50° C. for one hour and at 110° C. for two hours. A precipitate formed during storage of the reaction mixture in a refrigerator for three days. The precipitate was recovered by filtration and was recrystallized from water. Two crops of white crystals weighing 30.6 g and 10.5 g, respectively, were recovered. The wet methylenedithioacetic acid was dried in a heated dessicator and then in a vacuum dessicator. The dried white solid weighed 27.5 g, m.p. 120°–121.5° C.

To a stirred solution of 26.1 g (0.13 mole) of methylenedithioacetic acid in 200 ml of acetonitrile were added 31.9 g (0.29 mole) of ethyl bromide and 40.5 g (0.27 mole) of 1,8-diazabicyclo[5.4.0]undec-7-ene. The mixture was heated at 50° C. for eighteen hours. Water (800 ml) was added to the reaction mixture which was then extracted four times with 300 ml portions of diethyl ether. The combined extracts were washed successively with 300 ml portions of 5% aqueous sodium bicarbonate solution, water, and saturated aqueous sodium chloride solution. The diethyl ether solution was then dried over anhydrous magnesium sulfate. Evaporation of the solvent left a residue of diethyl methylenedithioacetate as a yellow oil weighing 28.9 g.

To a stirred mixture of 1.52 g (0.63 mole) of sodium hydride in 500 ml of diethyl ether under a nitrogen atmosphere was slowly added 13.8 g (0.30 mole) of absolute ethanol. After the addition was complete, the reaction mixture was refluxed for thirty minutes. Following removal of the heat source 15.0 g (0.059 mole) of diethyl methylenedithioacetate was added to the reaction mixture in one portion. The cloudy reaction mixture became clear briefly and then became cloudy within thirty seconds. After the reaction mixture had stirred at room temperature for twenty-four hours, 400 ml of 5% hydrochloric acid was added. The reaction mixture was separated, and the aqueous phase extracted twice with 150 ml portions of diethyl ether. The combined ether extracts were washed successively with 100 ml of water and 100 ml of a saturated aqueous solution of sodium chloride. After being dried over anhydrous magnesium sulfate, the solvent was evaporated under reduced pressure, leaving a yellow oil weighing 11.5 g as residue. This residue was placed on a column of silica gel and was eluted with ethyl acetate/hexane (25/75 v/v). Evaporation of the solvent from appropriately combined fractions yielded 9.4 g of 4-ethoxycarbonyl-1,3-dithiacyclohexan-5-one as a dark oil.

To a mixture of 10 ml ethylene glycol, 70 ml benzene, and 0.2 g p-toluenesulfonic acid was added 2.0 g (0.0097 mole) of 4-ethoxycarbonyl-1,3-dithiacyclohexan-5-one. The reaction was stirred at reflux for 96 hours during which time free water was continuously removed by a Dean-Stark trap. A 5% aqueous solution of sodium bicarbonate (150 ml) was added to the reaction mixture. After separating the organic phase from the aqueous phase, the latter was extracted twice with 75 ml of diethyl ether. The organic phase and the ether extracts were combined and were washed successively with 50 ml of aqueous 5% sodium bicarbonate solution, three times with 50 ml portions of water, and 50 ml of a saturated aqueous solution of sodium chloride. The solution was dried over anhydrous magnesium sulfate after which the solvent was evaporated under reduced pressure, leaving a yellow oil as a residue. After 48 hours storage at 0° C. the oil had crystallized to a yellow solid which was dried in a vacuum dessicator. The 6-ethoxycarbonyl-1,4-dioxa-7,9-dithiaspiro[4.5]decane was recovered as a yellow powder weighing 1.2 g.

To a solution of 0.4 g (0.010 mole) of sodium hydroxide in 15 ml of water and 10 ml of ethanol was added 1.2 g (0.0048 mole) of 6-ethoxycarbonyl-1,4-dioxa-7,9-dithiaspiro[4.5]decane. The reaction mixture was stirred at 60° C. for six hours. After distilling off the ethanol, the mixture was cooled in an ice/water bath. The solution was acidified with concentrated hydrochloric acid, causing a white solid to precipitate. The solid was collected by filtration, washed with water, and dried in a vacuum dessicator, yielding 1.0 g of 1,4-dioxa-7,9-dithiaspiro[4.5]decane-6-carboxylic acid as a whitish solid, m.p. 195°–197° C.

To a suspension of 0.75 g (0.0034 mole) of 1,4-dioxa-7,9-dithiaspiro[4.5]decane-6-carboxylic acid in 10 ml of water was added 0.1 ml of concentrated hydrochloric acid. The solution was vigorously stirred while refluxing for four hours. When the solution cooled, a white, crystalline precipitate appeared. This precipitate was collected by vacuum filtration. The solid was washed with cold water and was dried in a vacuum dessicator, yielding 0.4 g of 1,3-dithiacyclohexan-5-one as yellow crystals, m.p. 110°–112° C. The proton nmr spectrum was consistent with the proposed structure. Gas chromatographic analysis showed the compound to be 96.6% pure.

To a stirred suspension of 0.45 g (0.019 mole) of sodium hydride in tetrahydrofuran under a nitrogen atmosphere was added slowly 1.0 g (0.0074 mole) of 1,3-dithiacyclohexan-5-one. This mixture was stirred at room temperature until nitrogen evolution ceased. Then, 1.69 g (0.0090 mole) of O,O-diethyl phosphorothioic chloride was added to the reaction mixture causing it to burn light brown in color 0.5 hour after addition commenced. The reaction was complete after one hour. It was poured into 10% hydrochloric acid. The organic phase was separated from the aqueous phase. The latter was extracted three times with methylene chloride, and the combined extracts were washed successively with water, three times with an aqueous solution of sodium bicarbonate, and three times with a saturated aqueous solution of sodium chloride. The organic phase was dried over anhydrous magnesium sulfate and filtered. The solvent was evaporated under reduced pressure, leaving 1.99 g of light brown oil as a residue. This oil was passed through a short silica gel column, eluting with hexane/ethyl acetate (1/1 v/v). Removal of the solvent yielded O,O-diethyl O-(1,3-dithiacyclohex-4-en-5-yl)phosphorothioate as a yellow oil.

Analysis: Calc for $C_8H_{15}O_3PS_3$: C 33.55; H 5.28; Found: C 33.90; H 5.55.

nmr: 1.33(t, 6H), 3.4–3.5(m, 2H), 3.86(s, 2H), 4.0–4.5(m, 4H), 6.2(m, 1H).

EXAMPLE 17

Diethyl 1,4-Dithiacyclohept-5-en-6-yl Phosphate

A solution of 15.2 g (0.12 mole) of 1,3-dichloroacetone in 100 ml of diethyl ether was prepared. A second solution was prepared by diluting 55.1 ml of a 25% methanol solution of sodium methoxide (13.0 g, 0.24 mole) with 100 ml of methanol and adding 11.3 g (0.12 mole) of ethanedithiol with stirring under a nitrogen atmosphere at 0° C. The two solutions were added simultaneously under a nitrogen atmosphere to a flask containing 100 ml of diethyl ether and 600 ml of methanol. During the addition which required 1.5 hours the temperature was maintained at 8° C. The reaction mixture was poured into a mixture of 150 ml of diethyl ether, 200 ml of ice, and water. The organic phase was separated, and the aqueous phase was extracted four times with 150 ml portions of diethyl ether and three times with 100 ml portions of ethyl acetate. The extracts were combined with the organic phase and were washed with 200 ml of water and 200 ml of a saturated aqueous solution of sodium chloride. After being dried over anhydrous sodium sulfate, the solvent was evaporated under reduced pressure, leaving a yellow oil, a solid, and a seemingly immiscible liquid phase. The oil was dissolved in 100 ml of diethyl ether, and this solution was decanted from the polymeric solid. After removal of the solvent under reduced pressure, 15.0 g of 1,4-dithiacycloheptan-6-one was isolated as yellow liquid.

The 1,4-dithiacycloheptan-6-one was reacted with sodium hydride, and the product was reacted with O,O-diethyl phosphoric chloride to produce diethyl 1,4-dithiacyclohept-5-en-6-yl phosphate as a light yellow oil.

Analysis: Calc for $C_9H_{17}O_4PS_2$: C 38.02; H 6.02; Found: C 37.75; H 5.94.

nmr: 1.40(dt, 6H), 2.8–3.4(m, 4H, 3.73(s, 2H), 4.23(dq, 4H), 6.27(d, 1H).

EXAMPLE 21

Diethyl 1-Oxo-1,4-dithiacyclohept-5-en-6-yl Phosphate

To a solution of 1.9 g (0.0035 mole) of diethyl 1,4-dithiacyclohept-5-en-6-yl phosphate (Example 17) in a mixture of 10 ml of water and 20 ml of methanol was added portionwise 1.2 g (0.0039 mole) of potassium peroxymonosulfate. During the addition the solution was maintained at 0° C. The mixture was stirred for ten minutes after completion of addition. The reaction mixture was poured into 50 ml of water and was extracted twice with 50 ml of methylene chloride. The combined extracts were dried over anhydrous magnesium sulfate, and the solvent was evaporated under reduced pressure. The residue was combined with a similar residue from a previous experiment and was subjected to column chromatography on silica gel using acetone as eluant. Evaporation of the solvent yielded 0.90 g of diethyl 1-oxo-1,4-dithiacyclohept-5-en-6-yl phosphate.

Analysis: Calc for $C_9H_{17}O_5PS_2$: C 35.99; H 5.71; Found: C 35.65; H 5.44.

nmr: 1.40(dt, 6H), 2.6–3.5(m, 4H) 3.8–4.6(m, 6H), 6.60(d, 1H).

Other phosphoric esters within the scope of this invention are described in Table 1, the structure of the esters being confirmed by elemental analysis and proton nmr spectra.

In normal use of the phosphoric esters of the present invention, the esters ususally will not be employed free from admixture or dilution, but ordinarily will be used in a suitable formulated composition compatible with the method of application and comprising an insecticidally or acaricidally effective amount of phosphoric ester. The esters of this invention, like most pesticidal agents, may be blended with the agriculturally acceptable surface-active agents and carriers normally employed for facilitating the dispersion of active ingredients, recognizing the accepted fact that the formulation and mode of application of a pesticide may affect the activity of the material. The present phosphoric esters may be applied, for example, as sprays, dusts, or granules to the area where pest control is desired, the type of application varying of course with the pest and the environment. Thus, the esters of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the phosphoric esters. The granule particles are relatively large, a diameter of about 400–2500 microns typically. The particles are either impregnated with the ester from solution or coated with the phosphoric ester, adhesive sometimes being employed. Granules generally contain 0.05–10%, preferably 0.05–5%, active ingredient as the insecticidally or acaricidally effective amount.

Dusts are admixtures of the esters with finely divided solids such as talc, attapulgite clay, kiesel-guhr, pyrophyllite, chalk, diatomaceous earths, calcium phosphates, calcium and magnesium carbonates, sulfur, flours, and other organic and inorganic solids which act as carriers for the pesticide. These finely divided solids have an average particle size of less than about 50 microns. A typical dust formulation useful for controlling insects or acarids contain 1 part of phosphoric ester, such as diethyl 1,4-diethiacyclohept-5-en-6-yl phosphate, and 99 parts of talc.

The phosphoric esters of the present invention may be made into liquid concentrates by dissolution or emulsification in suitable liquids and into solid concentrates by admixture with talc, clays, and other known solid carriers used in the pesticide art. The concentrates are compositions containing, as an insecticidally or acaricidally effective amount, about 5–50% ester, such as diethyl 1,4-dithiacyclohept-5-en-6-yl phosphate, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects or acarids contains 1.5 parts each of sodium lignosulfonate and sodium laurylsulfate as wetting agents, 25 parts of diethyl 1,4-dithiacyclohept-5-en-6-yl phosphate, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the phosphoric ester with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters or polydydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the pesticidal composition.

Other useful formulations include simple solutions of the active ingredient in a solvent in which it is completely soluble at the desired concentration, such as acetone or other organic solvents.

An insecticidally or acaricidally effective amount of phosphoric ester in an insecticidal or acaricidal composition diluted for application is normally in the range of about 0.001% to about 8% by weight. Many variations of spraying and dusting compositions known in the art may be used by substituting the esters of this invention into compositions known or apparent in the art.

The insecticidal or acaricidal compositions of this invention may be formulated with other active ingredients, including other insecticides, nematicides, acaricides, fungicides, plant growth regulators, fertilizers, etc. In using the compositions to control agricultural pests, it is only necessary that an insecticidally or acaricidally effective amount of phosphoric ester be applied to the locus itself where control is desired, or to the soil in the vicinity of a plant locus. Such locus may, e.g., be the insects or acarids themselves, plants upon which the pests feed, or the pest habitat. When the locus is soil, e.g., soil in which agricultural crops are or will be planted, the active compound may be applied to and optionally incorporated into the soil. For most applications, an insecticidally or acaricidally effective amount will be about 100 g to 3000 g per hectare.

The activity of the phosphoric esters described above was evaluated as follows:

The efficacy of the esters against foliage-feeding insects was tested with 10% acetone-water solutions containing 1000 ppm ester sprayed on the test plants to run-off. Ten individuals of three insect species, southern armyworm (*Spodoptera eridania*), Mexican bean beetle (*Epilachna varivestis*), and pea aphid (*Acyrthosiphon pisum*) were infested on whole plants (pea aphid) or on leaves excised from the plant. The tests were enclosed in ice cream cups and stored for 48 hours, after which mortality of the insects was recorded. Pinto bean plants which had already been infested with twospotted spider mites (*Tetranychus urticae*) were sprayed with the 100 ppm acetone-water solutions. After 48 hours mortality was recorded. The results of these tests appear in Table 2.

The esters were tested as soil insecticides against southern corn rootworm larvae. Dried clay loam soil (15 g) was placed in a glass test tube completely covering a three-day old corn sprout. To the test tube was added 3 ml of an acetone/water solution containing 50 ppm of the test compound. The resulting concentration of the test compound in the soil was 10 ppm. The test tube was capped and held at room temperature for five hours after which five third-stage southern corn rootworm larvae (*Diabrotica undecimpunctata howardi* Barber) were added to the treated soil. The test tubes were kept at room temperature under continuous fluorescent light for 72 hours. During this time active compounds will protect the seedling from larval feeding, allowing it to grow to a height of 11–14 cm. Inactive compounds offer no protection to the seedling which is completely destroyed by the larvae. The test was run in duplicate, and the results appear in Table 2.

In investigations of systemic insecticidal activity, bean seedlings, 5–6 cm tall, were transplanted into a soil composed of three parts sand and one part peat moss in 7.6 cm plastic pots. After a two-day recovery period 25 ml portions of a 10% acetone-water solution containing the appropriate concentration of the test compound was poured over the surface of the soil, avoiding contact with the foliage. Three days later the plants were infested and mortality was determined in the same manner as foliar tests. The results appear in Table 3.

Esters of this invention were also evaluated for efficacy against nematodes in the soil. In these tests the esters were formulated as 5 weight percent dusts with the following composition:
Test compound: 5 parts
Base: 95 parts
96% attapulgite clay
2% highly purified sodium lignosulfonate (100%)
2% powdered sodium alkylnaphthalenesulfonate (75%)

The mixture was ground to a fine powder.

The formulated compound was then mixed with soil infested with root-knot nematodes (*Meloidogyne incognita*) at 25 ppm (weight test compound/weight of soil) or lower. A young tomato plant was planted in each pot containing this treated soil. Young tomato plants were also planted in pots containing infested soil which has not been treated with the compounds (control plants). Both sets of pots were maintained in the greenhouse for two weeks, after which the roots of all plants were examined. The treated plants were compared with the control plants and rated according to the following system:

Knot Index

4—No control—amount of swellings equivalent to that developed on the roots of the untreated check plants.
3—Amount of swellings 25% less than that developed on the roots of the untreated check plants.
2—Amount of swellings 50% less than that developed on the roots of the untreated check plants.
1—Amount of swellings 75% less than that developed on the roots of the untreated check plants.
0—No swellings—complete control.

When the control observed was between 1 and 0 the Knot Index was subdivided to indicate how close the control was to 75% or to 100%. For this subdivision numbers between 0 and 1 were used as follows:
0.8: 80% control
0.5: 90% control
0.4–0.1: 95–99% control The knot index for the untreated check was 4.0. The test results are given in Table 4.

Esters of this invention also displayed activity in the soil against the soybean cyst nematode (*Heterodera glycines*), stunt nematode (*Tylenchorhynchus claytoni*), and the lesion nematode (*Pratylenchus penetrans*).

TABLE 1

Other Dithiacycloalkenyl Phosphoric Esters

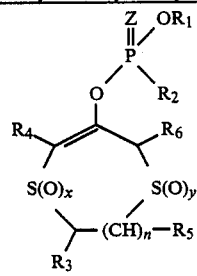

| Ex. | $R_1$ | $R_2$ | $R_3$ | $R_4$ | $R_5$ | $R_6$ | Z | n | x | y |
|---|---|---|---|---|---|---|---|---|---|---|
| 1 | $C_2H_5$ | $OC_2H_5$ | H | H | H | H | O | 0 | 0 | 0 |
| 3 | $C_2H_5$ | S—s-$C_4H_9$ | H | H | H | H | S | 0 | 0 | 0 |
| 4 | $C_2H_5$ | $OC_2H_5$ | $CH_3$ | H | H | H | O | 0 | 0 | 0 |
| 5 | $C_2H_5$ | $OC_2H_5$ | $CH_3$ | H | H | H | S | 0 | 0 | 0 |
| 9 | $C_2H_5$ | $OC_2H_5$ | phenyl | H | H | H | O | 0 | 0 | 0 |

TABLE 1-continued
Other Dithiacycloalkenyl Phosphoric Esters

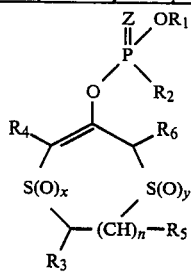

| Ex. | $R_1$ | $R_2$ | $R_3$ | $R_4$ | $R_5$ | $R_6$ | Z | n | x | y |
|---|---|---|---|---|---|---|---|---|---|---|
| 10 | $C_2H_5$ | $OC_2H_5$ | phenyl | H | H | H | S | 0 | 0 | 0 |
| 15 | $CH_3$ | $OCH_3$ | H | H | H | H | O | 1 | 0 | 0 |
| 16 | $CH_3$ | $OCH_3$ | H | H | H | H | S | 1 | 0 | 0 |
| 18 | $C_2H_5$ | $OC_2H_5$ | H | H | H | H | S | 1 | 0 | 0 |
| 19 | $C_2H_5$ | $S-s-C_4H_9$ | H | H | H | H | S | 1 | 0 | 0 |
| 20[b] | $C_2H_5$ | $OC_2H_5$ | $CH_3$/H | H | H/$CH_3$ | H | O | 1 | 0 | 0 |
| 22 | $C_2H_5$ | $OC_2H_5$ | H | H | H | H | O | 1 | 1 | 1 |
| 23 | $C_2H_5$ | $OC_2H_5$ | H | H | H | H | O | 1 | 1 | 2 |
| 24 | $C_2H_5$ | $OC_2H_5$ | H | H | H | H | O | 2 | 0 | 0 |
| 25 | $C_2H_5$ | $OC_2H_5$ | H | H | H | H | S | 2 | 0 | 0 |
| 26 | $CH_3$ | $OC_2H_5$ | H | H | H | H | O | 1 | 0 | 0 |
| 27 | $CH_3$ | $SC_2H_5$ | H | H | H | H | O | 1 | 0 | 0 |
| 28 | $C_2H_5$ | $SC_2H_5$ | H | H | H | H | O | 1 | 0 | 0 |
| 29 | $C_2H_5$ | $S-i-C_3H_7$ | H | H | H | H | O | 1 | 0 | 0 |
| 31 | $CH_3$ | $OCH_3$ | H | H | H | H | O | 1 | 0 | 1 |
| 32 | $C_2H_5$ | $OC_2H_5$ | H | H | H | H | S | 1 | 0 | 1 |
| 33 | $C_2H_5$ | $OC_2H_5$ | H | H | H | H | O | 1 | 0 | 2 |
| 34 | $C_3H_7$ | $SC_2H_5$ | H | H | H | H | O | 1 | 0 | 0 |
| 36[a] | $CH_3$ | $OCH_3$ | H | $CH_3$/H | H | H/$CH_3$ | O | 1 | 0 | 0 |
| 37[a] | $CH_3$ | $OCH_3$ | H | $CH_3$/H | H | H/$CH_3$ | O | 1 | 0 | 0 |
| 38[b] | $CH_3$ | $OCH_3$ | $CH_3$/H | H | H/$CH_3$ | H | O | 1 | 0 | 0 |
| 39[b] | $CH_3$ | $OCH_3$ | $C_2H_5$/H | H | H/$C_2H_5$ | H | O | 1 | 0 | 0 |
| 40[b] | $CH_3$ | $OCH_3$ | $C_2H_5$/H | H | H/$C_2H_5$ | H | S | 1 | 0 | 0 |
| 41[b] | $C_2H_5$ | $OC_2H_5$ | $C_2H_5$/H | H | H/$C_2H_5$ | H | O | 1 | 0 | 0 |
| 42[b] | $C_2H_5$ | $OC_2H_5$ | $C_2H_5$/H | H | H/$C_2H_5$ | H | S | 1 | 0 | 0 |
| 43[b,c] | $C_2H_5$ | $OC_2H_5$ | $C_2H_5$/H | H | H/$C_2H_5$ | H | O | 1 | 0/1 | 1/0 |
| 44[b,d] | $C_2H_5$ | $OC_2H_5$ | $C_2H_5$/H | H | H/$C_2H_5$ | H | O | 1 | 0/1 | 1/0 |
| 45 | $CH_3$ | $OCH_3$ | $CH_3$ | H | $CH_3$ | H | O | 1 | 0 | 0 |
| 46 | $C_2H_5$ | $OC_2H_5$ | $CH_3$ | H | $CH_3$ | H | O | 1 | 0 | 0 |
| 47 | $C_2H_5$ | $OC_2H_5$ | $CH_3$ | H | $CH_3$ | H | S | 1 | 0 | 0 |

[a] Mixtures of isomers in which either $R_4$ or $R_6$ is $CH_3$; 70% and 91% of Examples 36 & 37, respectively, are the $R_4 = CH_3$ isomer.
[b] Mixtures of isomers in which either $R_3$ or $R_5$ is $CH_3$ or $C_2H_5$; 50% of Examples 39, 40, 41, 42, 43, and 44 are the $R_3 = C_2H_5$ isomer; 50% of Examples 20 and 38 are the $R_3 = CH_3$ isomer.
[c] Mixture of three isomers.
[d] Mixture of two isomers.

TABLE 2

| Cpd. of Ex. | Insecticidal Efficacy Foliar[a] (percent mortality) | | | | Soil[b] SCR |
|---|---|---|---|---|---|
| | MBB | PA | SAW | TSM | |
| 1 | 50 | 100 | 100 | 100 | I |
| 2 | 80 | 100 | 0 | 100 | A |
| 3 | 100 | 90 | 0 | 100 | A |
| 4 | 50 | 100 | 0 | 100 | A |
| 5 | 95 | 100 | 50 | 100 | A |
| 9 | 0 | 100 | 40 | 100 | I |
| 10 | 35 | 100 | 40 | 100 | I |
| 15 | 50 | 0 | 0 | 100 | A |
| 16 | 100 | 100 | 50 | 100 | A |
| 17 | 75 | 100 | 30 | 100 | I/A[c] |
| 18 | 100 | 100 | 100 | 100 | A |
| 19 | 60 | 100 | 100 | 100 | A |
| 20 | 100 | 95 | 35 | 100 | A |
| 21 | 50 | 100 | 0 | 100 | A |
| 22 | 45 | 100 | 0 | 100 | I |
| 23 | 0 | 0 | 0 | 0 | I |
| 24 | 80 | 100 | 0 | 100 | A |
| 25 | 100 | 100 | 20 | 100 | A |
| 26 | 100 | 100 | 50 | 100 | A |
| 27 | 100 | 100 | 0 | 100 | A |
| 28 | 100 | 100 | 60 | 100 | A |
| 29 | 100 | 100 | 0 | 100 | A |
| 31 | 100 | 100 | 0 | 100 | A |
| 32 | 100 | 100 | 0 | 100 | A |
| 33 | 100 | 75 | 55 | 100 | A |
| 34 | 0 | 100 | 0 | 37[d] | A |
| 36 | 75 | 100 | 0 | 100 | A |
| 37 | 0 | 100 | 0 | 0[e] | A |
| 38 | 100 | 100 | 0 | 100 | A |
| 39 | 75 | 75 | 50 | 100 | A |
| 40 | 100 | 100 | 50 | 100 | A |
| 41 | 100 | 100 | 100 | 100 | A |
| 42 | 100 | 100 | 100 | 100 | A |
| 43 | 75 | 100 | 50 | 100 | A |
| 44 | 50 | 100 | 50 | 100 | A |
| 45 | 100 | 100 | 100 | 100 | A |
| 46 | 100 | 100 | 0 | 100 | A |

TABLE 2-continued

| Cpd. of Ex. | Insecticidal Efficacy Foliar[a] (percent mortality) | | | | Soil[b] |
|---|---|---|---|---|---|
| | MBB | PA | SAW | TSM | SCR |
| 47 | 100 | 100 | 75 | 100 | A |

[a]1000 ppm
MBB = *Epilachna varivestis* Mulsant
PA = *Acyrthosiphon pisum* Harris
SAW = *Spodoptera eridania* (Cramer)
TSM = *Tetranychus urticae* Koch
[b]10 ppm
SCR = *Diabrotica undecimpunctata howardi* Barber
A = active
I = inactive
[c]Two tests gave contradictory results
[d]Average of two tests
[e]Retests gave 100% kill at both 600 ppm and 64 ppm

TABLE 3

| Cpd. of Ex. | Appln. Rate (ppm) | Systemic Insecticidal Activity Percent Mortality[a] | | | |
|---|---|---|---|---|---|
| | | PA | SAW | TSM | MBB |
| 1 | 200 | 100 | 5 | 100 | |
| 4 | 500 | | 0 | | 100 |
| | 20 | 100 | | 100 | |
| 15 | 250 | 100 | 0 | 100 | 95 |
| 16 | 250 | 100 | 0 | 39 | 5 |
| 17 | 100 | 100 | 0 | 100 | 90 |
| 18 | 500 | 100 | 0 | 100 | 65 |
| 19 | 500 | | 0 | | 10 |
| | 250 | 0 | 0 | 0 | 0 |
| 20 | 500 | 100 | 0 | 100 | 100 |
| 21 | 250 | 100 | 40 | 100 | 100 |
| 22 | 250 | 80 | 0 | 0 | 0 |
| 23 | 500 | | 5 | | 0 |
| | 250 | 0 | 0 | 0 | 0 |
| 24 | 500 | 100 | 0 | 100 | 100 |
| 25 | 500 | 100 | 0 | 100 | 5 |
| 26 | 500 | | 0 | | 100 |
| | 64 | | | | 100 |
| | 50 | 100 | | 100 | |
| 27 | 500 | | 0 | | 20 |
| | 50 | 25 | | 6 | |
| 28 | 500 | | 0 | | 5 |
| | 50 | 10 | | 0 | |
| 29 | 500 | | 0 | | 15 |
| | 50 | 60 | | 4 | |
| 31 | 500 | | 90 | | 100 |
| | 50 | 100 | | 98 | |
| 32 | 100 | 95 | 0 | | 93 |
| | 50 | 68 | | 99 | 95 |
| 33 | 500 | | 0 | | 100 |
| | 50 | 50 | | 100 | 70 |
| 34 | 500 | | 0 | | 0 |
| 36 | 50 | 100 | | 100 | |
| 37 | 500 | | 0 | | 100 |
| | 16 | 55 | | 15 | |
| 38 | 500 | | 0 | | 95 |
| | 50 | 100 | | 100 | 0 |
| 39 | 500 | | 0 | | 60 |
| | 50 | 90 | | 100 | |
| 40 | 500 | | 0 | | 0 |
| | 50 | 35 | | 0 | |
| 41 | 500 | | 0 | | 90 |
| | 50 | 90 | | 40 | |
| 42 | 500 | | 0 | | 0 |
| | 50 | 0 | | 0 | |
| 43 | 500 | | 0 | | 100 |
| | 50 | 95 | | 0 | |
| 44 | 500 | | 0 | | 100 |
| | 50 | 15 | | 98 | 5 |
| 45 | 500 | | 0 | | 0 |
| | 50 | 93 | | 100 | |
| 46 | 500 | | 0 | | 0 |
| | 50 | 40 | | 13 | |
| 47 | 500 | | 0 | | 0 |

TABLE 3-continued

| Cpd. of Ex. | Appln. Rate (ppm) | Systemic Insecticidal Activity Percent Mortality[a] | | | |
|---|---|---|---|---|---|
| | | PA | SAW | TSM | MBB |
| | 50 | 85 | | 0 | |

[a]MBB = *Epilachna varivestis* Mulsant
PA = *Acyrthosiphon pisum* Harris
SAW = *Spodoptera eridania* (Cramer)
TSM = *Tetranychus urticae* Koch

TABLE 4

| Cpd. of Ex. | Nematicidal Efficacy (Tests Against Root-Knot Nematode) Knot Index | |
|---|---|---|
| | 25 ppm | 10 ppm |
| 1 | | 3.5 |
| 2 | 0[a] | 0 |
| 3 | 0.25 | 3.5 |
| 4 | | 2.5 |
| 5 | | 0 |
| 9 | 3.5 | 4.0 |
| 10 | 4 | |
| 15 | | 0.1 |
| 16 | | 0 |
| 17 | 0.80[a] | 0.60 |
| 18 | 3.5 | |
| 19 | | 0.90 |
| 20 | | 0.48 |
| 21 | | 0 |
| 22 | | 2.67 |
| 23 | | 3.75 |
| 24 | | 0.25 |
| 25 | | 0.13 |
| 27 | | 2.5 |
| 28 | | 2.0 |
| 29 | | 3.5 |
| 32 | | 0.18 |
| 33 | | 1.67 |
| 34 | | 4.0 |
| 38 | | 0.62 |
| 40 | | 0 |
| 41 | | 0 |
| 42 | | 0.07 |
| 43 | | 1.27 |
| 45 | | 0.33 |
| 46 | | 0 |

[a]Cucumber, rather than tomato

What is claimed is:

1. A dithiacycloalkenyl phosphoric ester of the formula

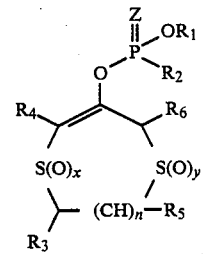

wherein
$R_1$ is lower alkyl;
$R_2$ is lower alkoxy or lower alkylthio;
$R_3$ is hydrogen, lower alkyl or phenyl;
$R_4$, $R_5$ and $R_6$ are independently hydrogen or lower alkyl;
Z is oxygen or sulfur;
x is 0 or 1;

y is 0, 1 or 2; and n is 0, 1 or 2; with the proviso that x+y is less than 3.

2. An ester of claim 1 wherein $R_3$ and $R_5$ are independently hydrogen or methyl, $R_4$ and $R_6$ are hydrogen, y is 0, and n is 1.

3. An ester of claim 2 wherein $R_2$ is lower alkoxy.

4. An ester of claim 2 wherein $R_1$ is other than methyl and $R_2$ is other than methoxy.

5. An ester of claim 1 selected from diethyl 1,4-dithiacyclohept-5-en-6-yl phosphate, diethyl 1-oxo-1,4-dithiacyclohept-5-en-6-yl phosphate, and dimethyl 1-oxo-1,4-dithiacyclohept-5-en-6-yl phosphate.

6. O,O-Diethyl O-(1,3-dithiacyclohex-4-en-5-yl)phosphorothioate, an ester of claim 1.

7. Dimethyl 1,4-dithiacyclohept-5-en-6-yl phosphate, an ester of claim 1.

8. Diethyl 1,4-diethiacyclohept-5-en-6-yl phosphate, an ester of claim 1.

9. O,I-Diethyl O-(1,4-dithiacyclohept-5-en-6-yl)phosphorothioate, an ester of claim 1.

10. Diethyl 2-methyl-1,4-dithiacyclohept-5-en-6-yl phosphate, an ester of claim 1.

11. Diethyl 3-methyl-1,4-dithiacyclohept-5-en-6-yl phosphate, an ester of claim 1.

12. Diethyl 1-oxo-1,4-dithiacyclohept-5-en-6-yl phosphate, an ester of claim 1.

13. Dimethyl 1-oxo-1,4-dithiacyclohept-5-en-6-yl phosphate, an ester of claim 1.

14. 5-Methyl-1,4-dithiacyclohept-5-en-6-yl phosphate, an ester of claim 1.

15. 7-Methyl-1,4-dithiacyclohept-5-en-6-yl phosphate, an ester of claim 1.

16. Dimethyl 2-methyl-1,4-dithiacyclohept-5-en-6-yl phosphate, an ester of claim 1.

17. Dimethyl 3-methyl-1,4-dithiacyclohept-5-en-6-yl phosphate, an ester of claim 1.

18. An agricultural composition comprising in admixture with an agriculturally acceptable carrier an insecticidally or acaricidally effective amount of at least one dithiacycloalkenyl phosphoric ester of the formula

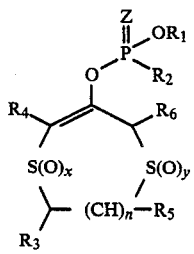

wherein $R_1$ is lower alkyl;

$R_2$ is lower alkoxy or lower alkylthio;

$R_3$ is hydrogen, lower alkyl or phenyl;

$R_4$, $R_5$ and $R_6$ are independently hydrogen or lower alkyl;

Z is oxygen or sulfur;

x is 0 or 1;

y is 0, 1 or 2; and n is 0, 1 or 2; with the proviso that x+y is less than 3.

19. A composition of claim 18 wherein $R_3$ and $R_5$ are independently hydrogen or methyl, $R_4$ and $R_6$ are hydrogen, y is 0 and n is 1.

20. A composition of claim 19 wherein $R_2$ is lower alkoxy.

21. A composition of claim 19 wherein $R_1$ is other than methyl and $R_2$ is other than methoxy.

22. A composition of claim 18 wherein said ester is selected from O,O-diethyl O-(1,3-dithiacyclohex-4-en-5-yl)phosphorothioate, dimethyl 1,4-dithiacyclohept-5-en-6-yl phosphate, diethyl 1,4-dithiacyclohept-5-en-6-yl phosphate, O,O-diethyl O-(1,4-dithiacyclohept-5-en-6-yl)phosphorothioate, diethyl 2-methyl-1,4-dithiacyclohept-5-en-6-yl phosphate, diethyl 3-methyl-1,4-dithiacyclohept-5-en-6-yl phosphate, diethyl 1-oxo-1,4-dithiacyclohept-5-en-6-yl phosphate, dimethyl 1-oxo-1,4-dithiacyclohept-5-en-6-yl phosphate, 5-methyl-1,4-dithiacyclohept-5-en-6-yl phosphate, 7-methyl-1,4-dithiacyclohept-5-en-6-yl phosphate, dimethyl 2-methyl-1,4-dithiacyclohept-5-en-6-yl phosphate, and dimethyl 3-methyl-1,4-dithiacyclohept-5-en-6-yl phosphate.

23. A composition of claim 22 wherein said ester is selcted from diethyl 1,4-dithiacyclohept-5-en-6-yl phosphate, diethyl 1-oxo-1,4-dithiacyclohept-5-en-6-yl phosphate, and dimethyl 1-oxo-1,4-dithiacyclohept-5-en-6-yl phosphate.

24. The method for controlling insects or acarids which comprises applying to the locus where control is desired an insecticidally or acaricidally effective amount of at least one dithiacycloalkenyl phosphoric ester of the formula wherein $R_1$ is lower alkyl;

$R_2$ is lower alkoxy or lower alkylthio;

$R_3$ is hydrogen, lower alkyl or phenyl;

$R_4$, $R_5$ and $R_6$ are independently hydrogen or lower alkyl;

Z is oxygen or sulfur;

x is 0 or 1;

y is 0, 1 or 2; and n is 0, 1 or 2; with the proviso that x+y is less than 3.

25. The method of claim 24 wherein $R_3$ and $R_5$ are independently hydrogen or methyl, $R_4$ and $R_6$ are hydrogen, y is 0, and n is 1.

26. The method of claim 25 wherein said locus is plant foliage and $R_2$ is lower alkoxy.

27. The method of claim 26 wherein said ester is selected from diethyl 1,4-dithiacyclohept-5-en-6-yl phosphate, diethyl 1-oxo-1,4-dithiacyclohept-5-en-6-yl phosphate, and dimethyl 1-oxo-1,4-dithiacyclohept-5-en-6-yl phosphate.

* * * * *